US006416967B2

(12) United States Patent
Kornblith

(10) Patent No.: US 6,416,967 B2
(45) Date of Patent: *Jul. 9, 2002

(54) METHOD OF USING MULTICELLULAR PARTICULATES TO ANALYZE MALIGNANT OR HYPERPROLIFERATIVE TISSUE

(75) Inventor: Paul L. Kornblith, Pittsburgh, PA (US)

(73) Assignee: Precision Therapeutics, Inc., Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/189,310

(22) Filed: Nov. 10, 1998

Related U.S. Application Data

(63) Continuation-in-part of application No. 08/679,056, filed on Jul. 12, 1996, now Pat. No. 5,728,541, which is a continuation-in-part of application No. 09/095,993, filed on Jun. 11, 1998, which is a continuation-in-part of application No. 09/039,957, filed on Mar. 16, 1998.

(51) Int. Cl.[7] .................................................. C12Q 1/02
(52) U.S. Cl. ........................................... 435/29; 435/30
(58) Field of Search ............................ 435/29, 30, 32, 435/240.2, 261, 803

(56) References Cited

U.S. PATENT DOCUMENTS

| 4,423,145 A | * | 12/1983 | Stampfer et al. .............. 435/32 |
| 4,937,187 A | * | 6/1990 | Rotman ........................ 435/30 |
| 5,242,806 A | * | 9/1993 | Yen-Maguire et al. ........ 435/32 |
| 5,270,172 A | * | 12/1993 | Morgan ........................ 435/29 |
| 5,607,918 A | * | 3/1997 | Eriksson et al. .............. 514/12 |
| 5,728,541 A | * | 3/1998 | Kornblith .................... 435/29 |
| 5,874,218 A | * | 2/1999 | Drolet et al. ................... 435/6 |
| 5,888,765 A | * | 3/1999 | Patterson et al. ........... 435/69.1 |
| 5,942,385 A | * | 8/1999 | Eriksson et al. ............. 435/325 |
| 5,972,639 A | * | 10/1999 | Parandoosh ................. 435/29 |
| 6,020,473 A | * | 2/2000 | Keyt et al. .................. 536/23.1 |

OTHER PUBLICATIONS

"Evaluation of Chemopreventive Agents in Different Mechanistic Classes Using a Rat Tracheal Epithelial Cell Cultrue Transformation Assay." Arnold et al., Cancer Research, vol. 55, pp. 537–543 (1995).

"Evidence of a Direct Relationship Between the Increase in the In Vitro Passage Number of Human Non–Small–Cell–Lung Cancer Primocultures and Their Chemosensitivity," Kruczynski et al., Anticancer Research, vol. 13, pp. 507–514 (1993).

Arnold, J. Evaluation of Chemopreventive Agents in Different Mechanistic Classes Using a Rat Tracheal Epithelial Cell Culture Transformation Assay. Cancer Research 55:537–543, Feb. 1995.*

Kruczynski A. Evidence of a Direct Relationship Between the Increase in the in Vitro Passage Number of Human Non–Small–Cell Lung Cancer Primocultures and Their Chemosensitivity. Anticancer Research 13:507–514, 1993.*

* cited by examiner

Primary Examiner—Ralph Gitomer
(74) Attorney, Agent, or Firm—Webb Ziesenheim Logsdon Orkin & Hanson, P.C.

(57) ABSTRACT

A comprehensive and integrated system for monitoring (identifying, tracking and analyzing) an individual patient's malignancy or hyperproliferative syndrome through the duration of a malignancy or hyperproliferative syndrome as to a specific patient is provided. Specimens of a patient's cells are collected and mechanically separated into cohesive multicellular particulates. A tissue culture monolayer is grown from the multicellular particulates to form a prime culture, and the tissue culture is monitored over a period of time. The invention allows for study of the effect of various treatment methods on cellular production of vascular endothelial growth factor.

22 Claims, 8 Drawing Sheets

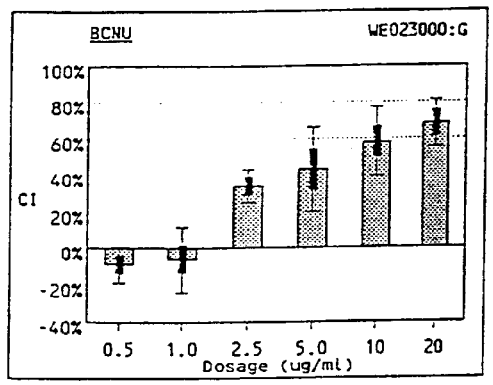
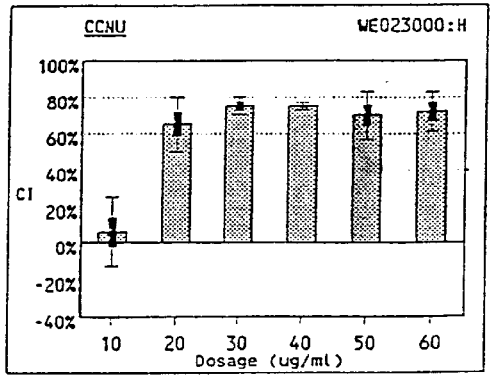
Fig. 3A　　Fig. 3B
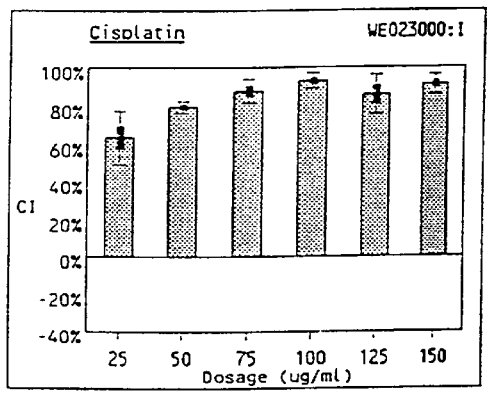
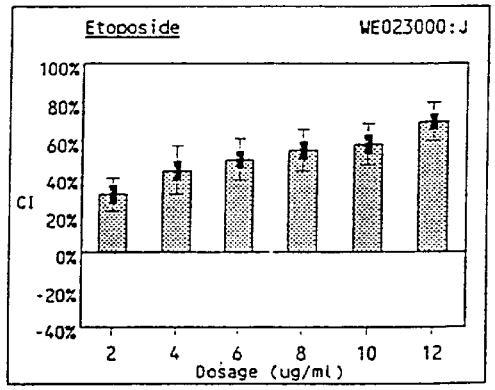
Fig. 3C　　Fig. 3D
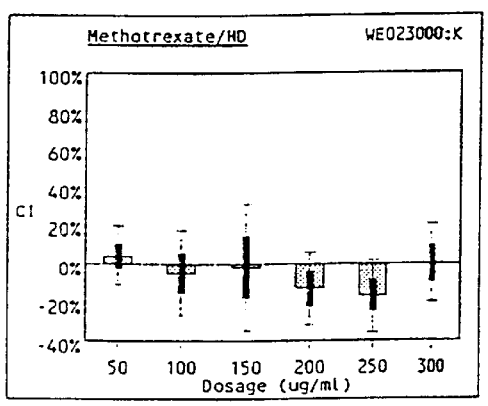
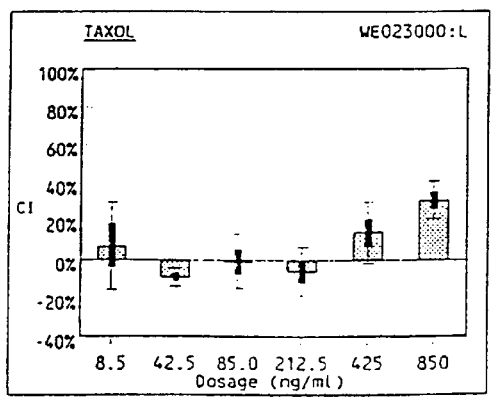
CI Chart Legend
　CI Value
　+/- 1 Standard Deviation
　+/- 1 Standard Error
Fig. 3E　　Fig. 3F CI Chart Legend
- CI Value
- $+/-$ 1 Standard Deviation
- $+/-$ 1 Standard Error

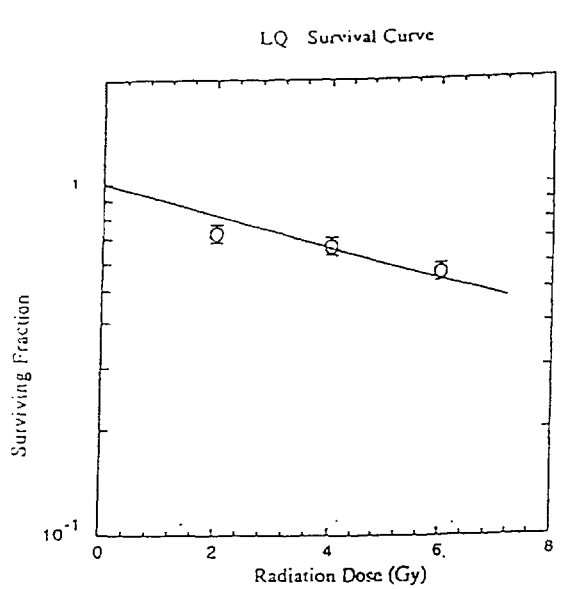
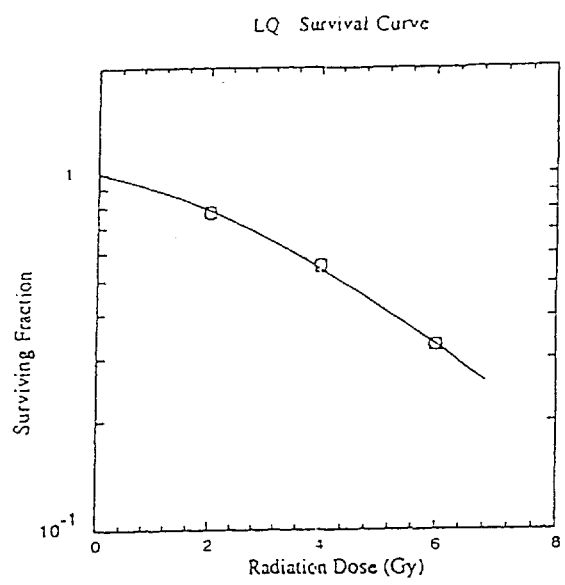
Fig. 6
Fig. 7

METHOD OF USING MULTICELLULAR PARTICULATES TO ANALYZE MALIGNANT OR HYPERPROLIFERATIVE TISSUE

RELATED APPLICATION

This is a Continuation-In-Part of U.S. application Ser. No. 08/679,056, filed Jul. 12, 1996, now U.S. Pat. No. 5,728,541, granted Mar. 17, 1998; U.S. application Ser. No. 09/095,993, filed Jun. 11, 1998; and U.S. application Ser. No. 09/039,957, filed Mar. 16, 1998.

BACKGROUND OF THE INVENTION

Field of the Invention

A system is provided for in vitro tracking of cancerous tissue over the course of the malignancy. The system provides a method for identifying the malignancy and for determining a patient's prognosis. Further, the system provides for assessing a malignancy's invasiveness, aggressiveness, growth rate, production of extracellular markers, possible side effects and for determining the efficacy on the malignancy of a given therapeutic regimen. The system also allows for generation of a therapeutic index, which serves as an indicator of a given therapy's effectiveness against the malignancy as compared to its undesirable side effects, such as lethality to a patient's normal cells.

INTRODUCTION

Tracking a malignancy in a patient according to prior art methods is an inaccurate process which involves identification of the malignancy through techniques including biopsy and subsequent histological, biochemical, and immunochemical techniques and regularly monitoring the malignancy's progression by invasive (i.e., biopsy) or noninvasive (i.e., x-ray, nuclear imaging, Magnetic Resonance Imaging (MRI) and Positron Emission Tomography (PET)) methods. These methods are often expensive, inconvenient, painful and usually involve hospital visits and safety risks. It is, therefore, desirable to reduce a patient's exposure to such methods. Furthermore, identification of a malignancy as a known variety of malignancy is often helpful in determining a suitable therapeutic approach and expected prognosis. However, even individually identifiable malignancies differ from patient-to-patient in their growth characteristics and in their responsiveness to treatment.

Determination of the growth rate, invasiveness and aggressiveness of a given malignancy is critical to prognosis and to the choice of therapies. A patient with a poor prognosis might be given a therapeutic regimen which might be more effective than another regimen but more risky to the patient. A patient with a better prognosis might be given a therapeutic regimen which is less aggressive and less risky to the patient, but which might not be as effective as often as a more dangerous therapy. Similarly, if a malignancy produces factors or creates conditions which cause a dangerous side effect, such as a thrombogenesis, the patient can be treated, preferably prophylactically, for the condition.

Current methodologies for determining growth rate, invasiveness, aggressiveness or which track the progression of a malignancy include biopsy and short-term culture, which can include drawing of blood or other bodily fluids, or semi- or non-invasive techniques such as x-ray and nuclear imaging. At any given time, a patient could be subject to multiple procedures, depending upon when the information is needed by the physician. Each procedure requires the presence of the patient and usually creates risk or pain. These procedures also can increase the stress level of the patient, which often is an exacerbating factor in cancer and associated prognoses. It is therefore, desirable to reduce the frequency of such procedures.

Identification of an effective therapeutic regimen is critically important to a patient. Often, once the malignancy is identified, a therapy is chosen based upon prior research on that type of malignancy and is not tailored to the sensitivities of the malignancy of a given patient. Often secondary therapies are needed because a first choice was ineffective. Valuable treatment time can be lost and a patient's life can be threatened.

All active agents including chemotherapeutic active agents are subjected to rigorous testing as to efficacy and safety prior to approval for medical use in the United States. Methods of assessing efficacy have included elaborate investigations of large populations in double blind studies as to a given treatment method and/or active agent, with concomitant statistical interpretation of the resulting data, but these conclusions are inevitably generalized as to patient populations taken as a whole. In many pharmaceutical disciplines and particularly in the area of chemotherapy, however, the results of individual patient therapy may not comport with generalized data—to the detriment of the individual patient. The need has been long recognized for a method of assessing the therapeutic potential of active agents, including but not limited to chemotherapeutic agents, for their efficacy as to a given individual patient, prior to the treatment of that patient. This need also applies to assessing the therapeutic potential as to radiation therapies, combined radiation/drug therapies and cellular immunotherapies.

Prior art assays already exist which expose malignant tissue of various types to a plurality of active agents, for the purpose of assessing the best choice for therapeutic administration. For example, in Kruczynski, A., et al., "Evidence of a direct relationship between the increase in the in vitro passage number of human non-small-cell-lung cancer primocultures and their chemosensitivity," *Anticancer Research*, vol. 13, no. 2, pp. 507–513 (1993), chemosensitivity of non-small-cell-lung cancers was investigated in vivo grafts, in vitro primocultures and in commercially available long-term cancer cell lines. The increase in chemosensitivity was documented and correlated with morphological changes in the cells in question. Sometimes animal model malignant cells and/or established cell cultures are tested with prospective therapy agents, see for example Arnold, J. T., "Evaluation of chemopreventive agents in different mechanistic classes using a rat tracheal epithelial cell culture transformation assay," *Cancer Res.*, vol. 55, no. 3, pp. 537–543 (1995).

In vitro prior art techniques present the further shortcoming that assayed cells do not necessarily express the cellular markers they would express in vivo. This is regrettable because the determination of expression of certain secreted or cellular markers, secreted factors or tumor antigens or lack thereof can be useful for both identification and therapeutic purposes. For instance, members of the fibrinolytic system such as urokinase-type plasminogen activator (u-PA) and plasminogen activator inhibitors type 1 (PAI-1) are up-regulated in malignant brain tumors. See, e.g., Jasti S. Rao, et al., "The Fibrinolytic System in Human Brain Tumors: Association with Pathophysiological Conditions of Malignant Brain Tumors," *Advances in Neuro-Oncology II*, Kornblith P L, Walker M D (eds) Futura (1997). Other secreted factors such as α-fetoprotein, carcinoembryonic antigen and transforming growth factors α and β have been found to be indicative of various cancers and/or cancer progression (see also, Singhal et al., "Elevated Plasma Osteopontin in Metastatic Breast Cancer Associated with Increased Tumor Burden and Decreased Survival," *Clinical Cancer Research*, vol. 3, 605–611, (April 1997); Kohno et al., "Comparative Studies of CAM 123-6 and Carcinoembryonic Antigen for the Serological Detection of Pulmonary Adenocarcinoma," *Cancer Detection and Prevention*, 21 (2): 124–128 (1997)). These examples are but a few of the many factors that may be used to identify diseased cells.

Cellular markers also include metastatic markers, indicative of metastatic potential, i.e., invasiveness and aggressiveness, which is relevant to the progression of a given malignancy and to a patient's prognosis. First, markers indicating the invasiveness of a given malignancy indicate the ability of the malignancy to infiltrate and to destroy adjacent tissue. As an example, for epithelial malignancies, invasiveness markers are indicative of the ability of the malignancy to infiltrate beneath the epithelial basement membrane. Invasiveness markers can include the presence of proteolytic enzymes or angiogenic factors. A second category of metastatic marker indicates growth conditions of the malignancy. For instance, a malignancy could require for instance a prostate-specific factor for growth. Invasiveness and aggressiveness factors are often present in serum or in tissue culture media.

Relevant to a patient's prognosis and, incidentally, to the identification of a malignancy is the presence of markers, cellular or secreted, which lead to complications beyond those involved with uncontrolled growth and invasion by a malignancy. For instance, secretion by the malignancy of thrombogenic substances by the malignancy can result in blood clotting, resulting in thrombophlebitis or other thrombotic events such as pulmonary thrombosis. Identification of a thrombotic potential indicates treatment (preferably prophylactically) with thrombolytic substances.

When a specific patient's cells are used in vitro assays in typical prior art processes the cells are harvested (biopsied) and trypsinized (connective tissue digested with the enzyme trypsin) to yield a cell suspension purportedly suitable for conversion to the desired tissue culture form. The in vitro tissue culture cell collections which result from these techniques are generally plagued by their inability accurately to imitate the chemosensitivity or therapeutic sensitivity of the original tumor or other cell biopsy. These collections often do not express cellular markers in the same manner that they would in vivo. A need thus remains for a technique of tissue culture preparation which provides cell cultures, allowing identification of a malignancy, accurate tracking of the malignancy's progress in a patient and therapy screening, in which, after simple preparation, the cell cultures react in a manner equivalent to their in vivo reactivity. The culture method would enable drug or chemotherapeutic agent, radiation therapy and/or cellular immunotherapy screening as to a particular patient for whom such screening is indicated.

A need also remains for a technique of tissue culture preparation which provides cell cultures for screening for expressed markers or factors where the cultured cells express the markers or factors in a manner indicative of their in vivo expression of the same. A further need also remains for a tissue culture preparation which allows for morphological study of the cells. Lastly, a need remains for a tissue culture system in which progression of an individual malignancy can be studied as indicative of the in vivo progression of the malignancy.

SUMMARY OF THE INVENTION

A comprehensive and integrated unified system for monitoring (i.e., identifying, tracking and analyzing) an individual patient's malignancy through the duration of a malignancy as to a specific patient is provided. The method of the present invention allows for initial identification of a malignancy, identification of malignancy-specific cellular or secreted markers, identification of cellular or secreted markers indicative of complications, study of the invasiveness and aggressiveness of the malignancy, study of the growth rate of the malignancy, study of the effect of therapies on the malignancy as compared to control cells of the same patient (chemosensitivity versus toxicity) and the identification of a therapeutic index (i.e., the ratio of chemosensitivity:toxicity), study of tumor morphology and study of histological and cytochemical markers.

The method of the present invention includes the steps of collecting a tissue sample or specimen of a patient's cells and separating the specimen into cohesive multicellular particulates (explants) of the tissue sample, rather than enzymatically digested cell suspensions or preparations. The cells are then grown as a tissue culture monolayer from the multicellular particulates to form a prime culture. A specimen can be taken from a patient at any relevant site, including but not limited to tissue, ascites or effusion fluid. Samples may also be taken from body fluid or exudates, as is appropriate. A tissue culture monolayer, designated as the prime culture, can be grown in any method known in the art for growing such a monolayer, for instance in tissue culture plates or flasks. If the malignant cells originate from solid tissue, however, the tissue must be subdivided into small pieces from which a tissue culture monolayer is then grown out.

Once a prime culture is established from a patient's malignancy, the prime culture can be maintained without any treatments beside normal feedings and passage techniques, as indicative of the growth of the malignancy absent treatment. However, subcultures of the prime culture are prepared so that the prime culture is preferably left untreated, and the cells of the prime culture are not affected by any testing. However, either the prime culture or a subculture thereof can be propagated as a reference culture. The reference culture is a culture which is treated with therapies reflective of a patient's actual treatments. For instance, if a patient is treated with a chemotherapeutic agent, the reference culture is treated with the same agent in the same concentration. The reference culture can be monitored genotypically or phenotypically to reflect actual progress of the malignancy in the patient. Treatment of the reference culture need not be limited to anticancer therapies, but can reflect all of a patient's treatments. For instance, thrombolytic or anti-thrombogenic treatments can be applied to the reference culture to reflect a patient's treatment. Subcultures of either the prime culture or the reference culture can be used for further analysis. Preferably, since the reference culture is indicative of the current state of a malignancy at a given time, subcultures of the reference culture are analyzed further. At various points in the passage of the control culture and the reference culture, aliquots of cells from those cultures can be stored cryogenically or otherwise.

The tissue sample technique of the present invention is also useful in assaying expression and/or secretion of various markers, factors or antigens present on or produced by the cultured cells. These assays can be used for diagnostic purposes for monitoring the applicability of certain candidate therapeutic or chemotherapeutic agents or for monitoring the progress of treatment of the cancer with those agents.

A method for identifying and monitoring progress of a malignancy in an individual patient is provided including the steps of inoculating cells from either the prime culture, the reference culture or a subculture of the prime culture or of the reference culture into a plurality of segregated sites; treating the plurality of sites with at least one treating means or therapy, followed by assessment of sensitivity of cells in the site to the treating means; collecting a specimen of a patient's non-malignant cells; separating the non-malignant cells into cohesive multicellular particles; growing a tissue culture monolayer from the multicellular particulates of non-malignant cells to form a control culture; inoculating the control culture in a plurality of non-segregated sites; treating the plurality of segregated sites of the control culture with the same treating means as the segregated sites of the prime culture or a subculture thereof, followed by assessment of the sensitivity of the segregated cells of the control culture to the treating means; and comparing the sensitivity of the segregated cells of the prime culture or a subculture thereof with the sensitivity of the segregated cells of the control culture to the treating means. The assessments described above are calculations of the percentage or fraction of cells sensitive, or insensitive, to the treatment and the method further includes the step of creating a therapeutic index of a ratio of one of the percentage of or the fraction of sensitive cells or insensitive cells in the segregated cells of the control culture to one of the percentage of or the fraction of sensitive cells or insensitive cells in the segregated cells of the prime culture or subculture thereof.

Lastly, a method for treating a patient having a malignancy is provided, including the steps of: analyzing a patient's cells prepared according to the above-described methods for malignancy-associated markers; determining a therapeutic regimen according to the results of the analysis; and treating a patient according to the regimen. The method can further include the step of treating one of either cells cultured as a subculture of the prime culture or cells of the prime culture according to the regimen as representative of the patient's malignancy. Lastly, the method further includes determining a therapeutic index for each treating means as described above.

When applicable, cultures can be grown in a readable (scannable) plate and to determine percent confluence of the cells or any other parameter which can be determined in such a manner. The scanner can be operably linked with a computer or CPU to automatically input data into the computer or CPU. The computer or CPU can be programmed to automatically calculate a therapeutic index (or other relevant indices) based upon the data provided by the scanner. Alternatively, the data can be entered manually into the programmed computer or CPU to calculate the index.

BRIEF DESCRIPTION OF THE DRAWINGS

FIGS. 2A–2F and 3A–3F show short-term and long-term assays for a first patient.

FIGS. 4A–4F and 5A–5F show short-term and long-term assays for a second patient.

FIGS. 6 and 7 show two radiation dose versus surviving fraction curves for two glioblastoma cell lines. Cells were irradiated in microtiter plates and assayed four days post-irradiation.

DETAILED DESCRIPTION OF THE PREFERRED EMBODIMENTS

Figure 1A:
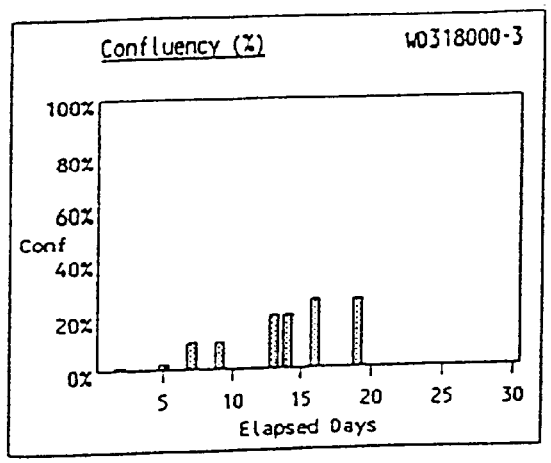
FIGS. 1A, 1B and 1C are graphs of the growth rates of three independent cell cultures.

The present invention is an improved and unified system for monitoring the progression of an individual malignancy and for identifying cellular and secreted markers, markers indicative of certain side effects of the malignancy and for screening multiple candidate therapeutic or chemotherapeutic agents for efficacy and long term effect as to a specific patient. In the method, a tissue sample from the patient is harvested, cultured and separately exposed to a plurality of treatments and/or therapeutic agents for the purpose of objectively identifying the best treatment for the cultured cells obtained from the patient. The culture techniques of the present invention also result in a monolayer of cells that express cellular markers, secreted factors and tumor antigens in a manner representative of their expression in vivo. Specific method innovations such as tissue sample preparation techniques render this method practically as well as theoretically useful. One particularly important tissue sample preparation technique is the initial preparation of cohesive multicellular particulates of the tissue sample, rather than enzymatically dissociated cell suspensions or preparations, for initial tissue culture monolayer preparation. With respect to the culturing of malignant cells, for example, it is believed (without any intention of being bound by the theory) that by maintaining the malignant cells within a multicellular particulate of the originating tissue, growth of the malignant cells themselves is facilitated versus the overgrowth of fibroblasts or other cells which tends to occur when suspended tumor cells are grown in culture. Practical monolayers of cells may thus be formed to enable meaningful screening of a plurality of treatments and/or agents as well as meaningful identification of cellular markers. In the drug assays, growth of cells is monitored to ascertain the time to initiate the assay and to determine the growth rate of the cultured cells; sequence and timing of drug addition is also monitored and optimized. By subjecting uniform samples of cells to a wide variety of active agents (and concentrations thereof), the most efficacious agent can be determined. For assays concerning cancer treatment, a two-stage evaluation is contemplated in which both acute cytotoxic and longer term inhibitory effects of a given anticancer agent are investigated.

With regard to the identification of expressed cellular markers, secreted factors or tumor antigens, with the initial culturing of the multicellular particulates it is believed (without any intention of being bound by the theory) that because the cells are grown under conditions closer to those found in vivo, the cells express their cellular markers, secreted factors and tumor antigens in a manner more closely resembling their expression in vivo. By assaying the culture media obtained from growing a monolayer according to the inventive method or by histochemically and/or immunohistochemically assaying the cells grown under such conditions, a more accurate profile of the cellular markers or factors is obtained.

Thus, a comprehensive and integrated system for identifying, tracking and analyzing an individual patient's malignancy through the duration of the malignancy and thereafter is provided. The method of the present invention allows for initial identification of a malignancy, identification of malignancy-specific cellular or secreted markers, identification of cellular or secreted markers indicative of complications, study of the invasiveness and aggressiveness of the malignancy, study of the growth rate of the malignancy, study of the effect of therapies on the malignancy as compared to control cells of the same patient (chemosensitivity and/or radiosensitivity versus toxicity) and the identification of a therapeutic index (i.e., the ratio of chemosensitivity:toxicity), study of tumor morphology and study of histological, cytochemical and immunocytochemical markers.

The method of the present invention includes the steps of collecting a tissue sample or specimen of a patient's cells and separating the specimen into cohesive multicellular particulates (explants) of the tissue sample, rather than enzymatically digested cell suspensions or preparations. The cells are then grown as a tissue culture monolayer from the multicellular particulates to form a prime culture. A specimen can be taken from a patient at any relevant site, including but not limited to tissue, ascites or effusion fluid. Samples may also be taken from body fluid or exudates, as is appropriate. A tissue culture monolayer can be grown in any method known in the art for growing such a monolayer, for instance in tissue culture plates or flasks.

Once a prime culture is established from a patient's malignancy, the prime culture can be maintained without any treatments beside normal feedings and passage techniques, as indicative of the growth of the malignancy absent treatment with a therapeutic regimen. Subcultures of the prime culture are prepared so that the cells of the prime culture are not affected by any subsequent testing or treatments. Although prime culture is preferably left untreated, either the prime culture or a subculture thereof can be propagated as a reference culture. The reference culture is a culture which is treated with therapies reflective of a patient's actual treatment regimen. For instance, if a patient is treated with a chemotherapeutic agent, the reference culture is treated with the same agent in the same concentration. The reference culture can be monitored genotypically or phenotypically to reflect actual progress of the malignancy in the patient. Treatment of the reference culture need not be limited to anticancer therapies, but can reflect all of a patient's treatments. For instance, thrombolytic or anti-thrombogenic treatments, can be applied to the reference culture to reflect a patient's treatment. Subcultures of either the prime culture or the reference culture can be used for further analysis. Preferably, since the reference culture is indicative of the current state in a patient of a malignancy, subcultures of the reference culture are analyzed. At various points in the passage of the control culture and the reference culture, aliquots of cells from those cultures can be stored cryogenically, or otherwise.

An important further aspect of the present invention is to provide a system for screening specific tissue samples from individual patients for expressed cellular markers, secreted factors or antigens, including tumor antigens, characteristic of the tissue sample. A tissue sample from a patient is harvested and grown in a monolayer culture as described above. Culture medium in which the cultures or subcultures thereof are assayed for the presence or absence of certain factors, such as secreted tumor antigens such as PAI-1, u-PA, cancer associated serum antigen (CASA) or carcinoembryonic antigen (CEA). These factors may be detected through use of standard assays such as radioimmunoassay (RIA) or enzyme-linked immunosorbent assay (ELISA), although other assays known to those skilled in the art may be used to detect and/or to quantify the soluble factors. The cell cultures grown in this manner may also be assayed histochemically and or immunohistochemically for identification or quantification of cellular or membrane-bound markers. Examples of such markers include, without limitation, CEA, tissue polypeptide specific antigen, (TPS) and mucin antigens, such as CA 15-3, CA 549, CA 27.29 and MCA. By screening tissue samples in this manner, for production of such factors, markers or antigens, the cultured cells may be further identified, aiding the physician in treatment strategies and as a prognosis indicator. Furthermore, by combining the use of the culture technique with assaying for such markers, factors and antigens, a treatment strategy for a disease state may be optimized and treatment progression may be monitored.

One important aspect of analyzing tissue culture medium is that complications of a malignancy can be predicted. For instance, one common complication is thrombogenesis. A propensity towards blood clot formation can be detected in tissue culture medium by identifying thrombogenic or procoagulant factors such as, without limitation, the Lewis Y antigen (Ley), HLA-DR and other tumor procoagulants, such as cancer procoagulant (CP) and tissue factor (TF). By identifying production of thrombogenic factors, a physician can prescribe drug and/or exercise regimens, as appropriate, to prevent life and/or limb-threatening clotting.

Cells and/or tissue culture media from any of the prime culture, the reference culture or subcultures thereof can be analyzed for tumor aggressiveness and invasiveness markers. Presence of these markers or absence thereof is highly relevant to a patient's prognosis. Furthermore, the effect of a given therapy on any of these markers can be analyzed. For instance, a tumor may produce angiogenic factors, such as, without limitation, vascular.endothelial growth factor (VEGF), which would lead a doctor to give a patient a less favorable prognosis. Other markers can include, without limitation, factors which allow cancer cells to affix to organs other than those from which the cancer cells derive, for instance, beta 3 integrin, which participates in the ability of melanoma cells to adhere to blood vessel walls. However, the effectiveness of therapies can be assessed if the presence of the angiogenic marker is analyzed in segregated sites according to the method of the present invention. A physician can suppress a malignancy by preventing expression of factors or markers which cause the malignancy's aggressiveness or invasiveness.

An important application of the present invention is the screening of chemotherapeutic agents and other antineoplastic therapies in tissue culture preparations of malignant cells from the patients from whom malignant samples are biopsied. Related anti-cancer therapies which also can be screened using the inventive system include radiation therapy and agents which enhance the cytotoxicity of radiation, as well as immunotherapeutic anti-cancer agents. Screening processes for treatments or therapeutic agents for nonmalignant syndromes are also embraced within this invention and include without limitation agents which combat hyper-proliferative syndromes, such as psoriasis, or wound healing agents. Nor is the present efficacy assay limited only to the screening of active agents which speed up (healing) or slow down (anti-cancer, anti-hyperproliferative) cell growth because agents intended to enhance or to subdue intracellular biochemical functions may be tested in the present tissue culture system also. For example, the formation or blocking of enzymes, neurotransmitters and other biochemicals may be screened with the present assay methods prior to treatment of the patient.

When a patient is to be treated for the presence of tumor, in the preferred embodiment of the present invention a tumor biopsy of >100 mg of non-necrotic, non-contaminated tissue is harvested from the patient by any suitable biopsy or surgical procedure known in the art. Biopsy sample preparation generally proceeds as follows under a Laminar Flow Hood which should be turned on at least 20 minutes before use. Reagent grade ethanol is used to wipe down the surface of the hood prior to beginning the sample preparation. The tumor is then removed, under sterile conditions, from the shipping container and is minced with sterile scissors. If the specimen arrives already minced, the individual tumor pieces should be divided into four groups. Using sterile forceps, each undivided tissue quarter is then placed in 3 ml sterile growth medium (Standard F-10 medium containing 17% calf serum and a standard amount of Penicillin and Streptomycin) and systematically minced by using two sterile scalpels in a scissor-like motion, or mechanically equivalent manual or automated opposing incisor blades. This cross-cutting motion is important because the technique creates smooth cut edges on the resulting tumor multicellular particulates. Preferably but not necessarily, the tumor particulates each measure 1 mm$^3$. After each tumor quarter has been minced, the particles are plated in culture flasks using sterile pasteur pipettes (9 explants per T-25 or 20 particulates per T-75 flask). Each flask is then labeled with the patient's code, the date of explanation and any other distinguishing data. The explants should be evenly distributed across the bottom surface of the flask, with initial inverted incubation in a 37° C. incubator for 5–10 minutes, followed by addition of about 5–10 ml sterile growth medium and further incubation in the normal, non-inverted position. Flasks are placed in a 35° C., non-$CO_2$ incubator. Flasks should be checked daily for growth and contamination. Over a period of a few weeks, with weekly removal and replacement of 5 ml of growth medium, the explants will foster growth of cells into a monolayer.

With respect to the culturing of malignant cells, it is believed (without any intention of being bound by the theory) that by maintaining the malignant cells within a multicellular particulate of the originating tissue, growth of the malignant cells themselves is facilitated versus the overgrowth of fibroblasts (or other unwanted normal cells) which tends to occur when suspended tumor cells are grown in culture.

The use of the above procedure to form a cell monolayer culture maximizes the growth of malignant cells from the tissue sample, and thus optimizes ensuing tissue culture assay of chemotherapeutic action of various agents to be tested. Enhanced growth of actual malignant cells is only one aspect of the present invention; however, another important feature is the growth rate monitoring system used to oversee growth of the monolayer once formed. Once a primary culture and its derived secondary monolayer tissue culture has been initiated, the growth of the cells is monitored to ascertain the time to initiate the chemotherapy assay and to determine the growth rate of the cultured cells.

Monitoring of the growth of cells is conducted by counting the cells in the monolayer on a periodic basis, without killing or staining the cells and without removing any cells from the culture flask. The counting may be done visually or by automated methods, either with or without the use of estimating techniques known in the art (counting in a representative area of a grid multiplied by number of grid areas, for example). Data from periodic counting is then used to determine growth rates which may or may not be considered parallel to growth rates of the same cells in vivo in the patient. If growth rate cycles can be documented, for example, then dosing of certain active agents can be customized for the patient. The same growth rate can be used to evaluate radiation treatment periodicity, as well. It should be noted that with the growth rate determinations conducted while the monolayers grow in their flasks, the present method requires no hemocytometry, flow cytometry or use of microscope slides and staining, with all their concomitant labor and cost.

Protocols for monolayer growth rate generally use a phase-contrast inverted microscope to examine culture flasks incubated in a 37° C. (5% $CO_2$) incubator. When the flask is placed under the phase-contrast inverted microscope, ten fields (areas on a grid inherent to the flask) are examined using the 10× objective, with the proviso that the ten fields should be non-contiguous, or significantly removed from one another, so that the ten fields are a representative sampling of the whole flask. Percentage cell occupancy for each field examined is noted, and averaging of these percentages then provides an estimate of overall percent confluency in the cell culture. When patient samples have been divided between two or among three or more flasks, an average cell count for the total patient sample should be calculated. The calculated average percent confluency should be entered into a process log to enable compilation of data—and plotting of growth curves—over time. Monolayer cultures may be photographed to document cell morphology and culture growth patterns.

The applicable formula is:

$$\text{Percent confluency} = \frac{\text{estimate of the area occupied by cells}}{\text{total area in an observed field}}.$$

As an example, therefore, if the estimate of area occupied by the cells is 30% and the total area of the field is 100%, percent confluency is 30/100, or 30.

Adaptation of the above protocol for non-tumor cells is straightforward and generally constitutes an equivalent procedure.

Active agent and/or radiation therapy screening using the cultured cells proceeds with subcultures of the prime culture or, preferably, of the reference culture. The screening can be carried out in an incubation flask, but generally proceeds using plates such as microtiter plates. In a chemotherapy/radiotherapy assay, it is desirable to grow a control culture of a patient's cells in a culture parallel to the reference or prime culture. The control culture can be grown from skin cells, as an easy source of non-malignant cells, from the same organ from which the malignant cells are derived, or from other sources, so long as the cells are typical of non-malignant cells of the patient.

The performance of the chemosensitivity/radiosensitivity assay used for screening purposes depends on the ability to deliver a reproducible cell number to each row in a plate and/or a series of plates, as well as the ability to achieve an even distribution of cells throughout a given well. The following procedure assures that cells are reproducibly transferred from flask to microtiter plates, and cells are evenly distributed across the surface of each well.

The first step in preparing the microtiter plates is, of course, preparing and monitoring the monolayer as described above. The following protocol is exemplary and susceptible of variation as will be apparent to one skilled in the art. Cells are removed from the culture flask and a cell pellet is prepared by centrifugation. The cell pellet derived from the monolayer is then suspended in 5 ml of the growth medium and mixed in a conical tube with a vortex for 6 to 10 seconds. The tube is then rocked back and forth 10 times. A 36 μl droplet from the center of the conical tube is pipetted onto one well of a 96 well plate. A fresh pipette is then used to pipette a 36 µl aliquot of trypan blue solution, which is added to the same well, and the two droplets are mixed with repeated pipette aspiration. The resulting admixture is then divided between two hemocytometer chambers for examination using a standard light microscope. Cells are counted in two out of four hemocytometer quadrants, under 10× magnification. Only those cells which have not taken up the trypan blue dye are counted. This process is repeated for the second counting chamber. An average cell count per chamber is thus determined. Using means known in the art, the quadrant count values are checked, logged, multiplied by $10^4$ to give cells/ml, and the total amount of fluid (growth medium) necessary to suspend remaining cell aliquots is calculated accordingly.

After the desired concentration of cells in medium has been determined, additional cell aliquots from the monolayer are suspended in growth medium via vortex and rocking and loaded into a Terasaki dispenser known in the art. Aliquots of the prepared cell suspension are delivered into the microtiter plates using Terasaki dispenser techniques known in the art. A plurality of plates may be prepared from a single cell suspension as needed. Plates are then wrapped in sterile wet cotton gauze and incubated in an incubator box by means known in the art.

After the microtiter plates have been prepared, exposure of the cells therein to active agent and/or radiation is conducted according to the following exemplary protocol. During this portion of the inventive assay, the appropriate amount of specific active agent is transferred into the microtiter plates prepared as described above. A general protocol, which may be adapted, follows. Each microtiter plate is unwrapped from its wet cotton gauze sponge and microscopically examined for cell adhesion. Control solution is dispensed into delineated rows of wells within the grid in the microtiter plate, and appropriate aliquots of active agent to be tested are added to the remaining wells in the remaining rows. Ordinarily, sequentially increasing concentrations of the active agent or higher doses of radiation being tested are administered into progressively higher numbered rows in the plate. The plates are then rewrapped in their gauze and incubated in an incubator box at 37° C. under 5% $CO_2$. After a predefined exposure time, the plates are unwrapped, blotted with sterile gauze to remove the agent, washed with Hank's Balance Salt Solution, flooded with growth medium, and replaced in the incubator in an incubator box for a predefined time period, after which the plates may be fixed and stained for evaluation.

Fixing and staining may be conducted according to a number of suitable procedures; the following is representative. After removal of the plates from the incubator box, culture medium is poured off and the plates are flooded with Hank's Balance Salt Solution. After repeated flooding (with agitation each time) the plates are then flooded with reagent grade ethanol for 2–5 minutes. The ethanol is then poured off. Staining is accomplished with approximately 5 ml of Giemsa Stain per plate, although volume is not critical and flooding is the goal. Giemsa stain should be left in place 5 min. ±30 seconds as timing influences staining intensity. The Giemsa stain is then poured off and the plates are dipped three times in cold tap water in a beaker. The plates are then inverted, shaken vigorously, and air dried overnight (with plate lids off) on a rack on a laboratory bench. Cells per well are then counted manually or by automated and/or computerized means, to derive data regarding chemosensitivity of cells at various concentrations of exposure. One particularly useful computer operating environment for counting cells is the commercially available OPTIMATE compiler, which is designed to permit an optical counting function well suited to computerized cell counting procedures and subsequent calculations.

The above procedures do not change appreciably when cell growth promoters are assayed rather than cell arresting agents such as chemotherapeutic or radiotherapeutic agents. The present assay allows cell death or cell growth to be monitored with equal ease. In any case, optimization of use of the present system will involve the comparative testing of a variety of candidate active agents for selection of the best candidate for patient treatment based upon the in vitro results. One particularly advantageous embodiment of the above described invention comprises a two-stage assay for cytotoxicity followed by evaluation of longer-term inhibitory effect. Chemotherapeutic agents may thus be evaluated separately for both their direct chemotherapeutic effect as well as for their longer duration efficacy.

As discussed in brief, above, in parallel with growth of the prime or reference culture, a control culture can be grown. The control culture is a culture of normal cells taken from the same patient from whom the prime culture is collected. The control culture can derive from an epithelial cell sample or can be collected from the same organ as the prime culture so long as the control culture contains no malignant cells. More than one control culture can be maintained. For instance, cultures of both normal skin cells and normal cells of an organ from which the malignancy is derived can be maintained. The value of maintaining a control culture is many fold. Primarily, the control culture serves as a negative control (or positive control, depending upon the marker to be analyzed) in the various analyses to be carried out on the prime culture, the reference culture or subcultures thereof.

A second value of the control culture is an indicator of toxicity, the toxicity or undesirable effects of a given therapy upon normal cells. For instance, in the segregated analysis of chemotherapeutic agents described above, concomitant analysis of the same agents on segregated sites of the control culture would yield an indication of cytotoxicity of the agent with regard to malignant cells versus the toxicity of the agent to control cells. A therapeutic index can be calculated based on the ratio of cytotoxicity to malignant cells to toxicity. Cytotoxicity and toxicity can be quantified as a percentage or fraction of cells killed by a given therapy, or as a percentage or fraction of cells surviving a given therapy. A therapeutic index is a ratio of these percentages or fractions and is reflective of the desirability of a given treatment in a patient. An optimal treatment would be maximally cytotoxic (or even cytostatic) to the malignant cells and minimally toxic to a patient's normal cells.

Other indices may be generated, depending upon the desired effect of a therapy. For instance, if a desired therapy is designed to up-regulate a malignancy-specific antigen to promote destruction of the malignancy by a patient's immune system, an index could be generated to discern a treatment which reflects maximal up-regulation of the antigen in the malignant cells and minimal or negative up-regulation in a patient's normal cells. A similar index can be calculated based upon down-regulation of a desired marker (i.e., an angiogenic factor) which can be assayed as either a secreted or a cellular marker and reflects maximal down-regulation of the marker with minimal toxicity or other undesirable effects on the control culture.

Often the diseased cells express a cellular marker that is indicative of a certain disease state or lack thereof. However, one aspect of the culture techniques of the present invention is that the cultured diseased cells do not necessarily have to be the cells expressing the factor to be assayed. One question that inevitably arises when considering whether a serum marker is indicative of a particular cancer cell is, which cells produce the marker, the cell or the tissue in which the cancer cells grow? See e.g. Singhal et al., p 610. By co-culturing the cancerous tissue within a multicellular particulate of its originating tissue, the cells (both the diseased cells or the surrounding cells) are better able to retain their production of characteristic markers.

Identification of one or more active agents or chemotherapeutic agents is peripheral to the present invention, which is intended for the efficacy screening of any or all of them as to a given patient. Literally any active agent may be screened according to the present invention; listing exemplary active agents is thus omitted here.

One important focus of the present invention thus includes the simplicity of the present system—cohesive multicellular particulates of the patient tissue to be tested are used to form cell monolayers; growth of those monolayers is monitored for accurate prediction of correlating growth of the same cells in vivo; and differing concentrations of a number of active agents may be tested for the purpose of determining not only the most appropriate agent but the most appropriate concentration of that agent for actual patient exposure (according to the calculated cell growth rates). It is also important to note, in the context of the invention, that the present system allows in vitro tests to be conducted in suspensions of tissue culture monolayers grown in nutrient medium under fast conditions (a matter of weeks), rather than with single cell progeny produced by dilution cloning over long periods of time. In some cases, the present invention is a two stage assay for both cytotoxicity and the longer-term growth inhibitory.

It is additionally possible to increase the value of the assay with the use of staining compositions and protocols designed to characterize the malignant cells thus grown. In other words, the tissue preparation and cell culturing technique itself offers a first assurance that the cells grown out of the tumor are really the malignant tumor cells and not fibroblasts or other nonmalignant cells of no diagnostic value. As a separate confirmation, the present staining compositions and protocols offer a second, independent assurance that the cells subject to diagnostic or prognostic assay are in fact malignant cells in culture. One important characterization has to do with the nature of the malignant cells as epithelial, which is in turn an indicator of the carcinoma type of malignancy. Other characterizations of malignant cells are intended to fall within the scope of the present invention as well, although the characterization of the cells as epithelial or not is of primary importance.

The technique is practiced as follows. The same cell culturing and well distribution process is used as in the cytotoxicity assay described above, but rather than exposing the cells to chemotherapeutic or other agents, the cells are instead fixed and stained. With the stain or stain cocktail described below, the epithelial cells are identified by their intermediate filaments and/or specific membrane antigens by means of a monoclonal antibody immunoperoxidase technique. The fixative used can be any fixative which does not alter the cellular molecular markers of interest. The fixed, stained cells are then counted. If the specimen is positive for epithelial cells, the process is complete. If the specimen is negative for epithelial cells, an independent fixing and staining process is subsequently completed, with fresh cells from identical wells, using Vimentin as a stain to confirm the non-epithelial nature of the cells.

The importance of having a stain or stain cocktail (i.e., antibody cocktail), as well as an overall protocol, for identifying epithelial cells in biopsies of malignant tumors is as follows. In the basic cytotoxicity assay, the tissue culture technique is designed to grow out the cells of the tumor of origin and in fact consistently does so. Despite such reliable predictability, however, the fact that the cells of the tumor of origin did in fact grow out, and not fibroblasts or other cells, must be confirmed with independent proof before the cells can be used with complete assurance in the appropriate patient assay(s). The present technology provides a means to obtain this confirmation, which in turn furthers the interests of good laboratory and medical practice.

As a general consideration, the staining compounds or compositions of interest for use in the present technology are those which bind with cellular molecular markers unique either to epithelial or to non-epithelial cells. A further aspect of the invention therefore inheres in the following two aspects: the improvement of the cytotoxicity assay by adding the epithelial staining protocol with any known epithelial stain; and the further improvement wherein specially designed stain cocktails maximize the likelihood that the presence of any known intermediate filament or specific membrane antigen, characteristic of epithelial cells, will be identified if present.

Many carcinomas are positive for any one of the intermediate filaments or specific membrane antigens characteristic of epithelial cells; virtually all if not all carcinomas are positive for one of a number of such intermediate filaments or specific membrane antigens. For example, "epithelial membrane antigen" (EMA) glycoproteins are known in the art and can be bound with various antiepithelial membrane antigen antibodies including monoclonal antibodies. Cytokeratin is another important epithelial cell marker and binding reagents including monoclonal antibodies are available which are specific to cytokeratin. While antisera can be raised in vivo against markers such as EMA glycoproteins and cytokeratin, as a practical matter commercially available polyclonal or monoclonal antibodies are used in the following protocols, with monoclonal antibodies being preferred.

Binding of the epithelial marker is revealed with associated staining procedures and reactions which give a visual indication that the marker binding took place. Those skilled in the art already appreciate various techniques already available—in the general field of "immunocytochemistry"—to reveal antibody-antigen re-actions. One known way to accomplish this visualization when antibody binding reagents are used is with the "labeled streptavidin procedure". In this procedure, after the specimen is exposed to antibodies specific to the target antigen, a secondary "link" antibody is added. The secondary biotinylated "link" antibody consists of anti-mouse and anti-rabbit antibodies which bind universally to most primary monoclonal or polyclonal antibodies. The "link" will also connect to the tertiary reagent (peroxidase-labeled streptavidin) through chemical bonding between the biotin on the secondary reagent and the streptavidin on the streptavidin/peroxidase conjugate. Staining is completed by incubating the specimen and primary, secondary and tertiary agents in the presence of a chromogen, so that the peroxidase and the chromogen form a visible precipitate. Alternatively, a fluorescein-based detection system can be used to visualize the primary antibody, or a third alternative known in the art as the digoxigenin-conjugated detection system may be used.

Of the various epithelial markers, three have received the most widespread attention in the literature: EMA glycoproteins, cytokeratin, and carcinoembryonic antigen. In the context of this invention, the first two are the most important because literally any epithelial cell will have at least either one EMA glycoprotein on the surface thereof or a cytokeratin intermediate filament present. Therefore, the present invention resides not only in binding and staining for an epithelial marker on the surfaces of the specimen cells, but in simultaneously assaying for either or both of EMA glycoprotein(s) and cytokeratin. The cocktails of the present invention therefore contain binding reagents for both EMA glycoproteins and cytokeratin and, importantly, are selected to include the most generally applicable binding reagents in combination so that the cocktail has the broadest binding scope possible. The cocktails identified in Examples 1 and 2, for example, represent a combination of two general binding reagents (containing a total of three monoclonal antibodies) for cytokeratin, admixed with a general binding reagent for EMA glycoprotein. The dual benefit of this admixture of general binding agents is that the incidence of false negatives for epithelial cells is minimized, and the visible staining reactions are generally stronger when the combined binding reagents are used in lieu of a single binding reagent.

Although the binding reagents and other reagents identified in the Examples are the preferred reagents for use in the context of the invention, the invention is intended to encompass epithelial-specific binding and staining reagents generally. These include, without limitation: Boehringer-Mannheim AE1 anti-cytokeratin antibody; Boehringer-Mannheim AE3 anti-cytokeratin antibody; Boehringer-Mannheim AE1/AE3 anti-cytokeratin antibody (AE1 and AE3 in admixture); Becton-Dickinson CAM 5.2 antibody, DAKO EMA antibody, Biomeda's Anti-Cytokeratin Cocktail CK22, Biomeda's Anti-Cytokeratin Cocktail CK23, Biomeda's Anti-Pan-Cytokeratin CK56, Biomeda's polyclonal goat or rabbit anti-cytokeratin antisera, ScyTek Laboratories' anti-EMA antigen antibody clone E29, and many others. Those skilled in the art and in possession of the guidance provided herein can readily determine alternative, equivalent binding and staining reagents and cocktails, to accomplish the disclosed result. These binding agents and cocktails may be used in combination with any known visualization system, such as the streptavidin, fluorescein- and digoxigenin-conjugated systems identified above.

As a control, Vimentin antibody is used as a binding alternative either in conjunction with binding and staining of the test cells, or subsequently thereto. In the context of this invention, Vimentin can be considered a binding reagent which is specific to non-epithelial cells of mesenchymal origin.

In a further aspect of the present invention, immunological markers may be monitored in applications requiring up- or down-regulation of such markers (i.e., Major histocompatibility complex molecules). This aspect of the present invention can be especially useful in transplantation applications where, for instance, through chemical or biological means rejection of transplanted cells is sought to be avoided by down-regulation of the various transplantation antigens present on the cells to be transplanted. The present invention would be especially useful in monitoring such immunoregulation.

Lastly, cell morphology can be assayed by culturing cells of, i.e., the prime culture or the reference culture, removing the cells from the surface upon which they grow, centrifuging cells into a loose pellet and growing the cell pellet over a defined time period. By growing cells in this manner, it is possible to view the cohesive morphology of cells in a cluster resembling a tumor.

EXAMPLE 1

Radiation Therapy

Separate 50 mg samples from residual tissue from specimens of three human glioblastomas and one human ovarian carcinoma were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours later, the cells were irradiated using a Siemens Stabilipan X-ray machine at 250 kVp, 15 mA with a dose rate of 75 rad/minute. For each radiation dose from 1 Gy to 6 Gy, cell number per well was monitored as a function of time through five days post-irradiation.

Cell number relative to controls was determined and survival curves were fit to the data. The rate of decrease in survival as a function of time was proportional to dose. A differential radiation response among the four cell lines was observed.

EXAMPLE 2

Immuno Therapy

Separate 50 mg samples from residual tissue from specimens of a human brain tumor, renal carcinoma, and breast carcinoma were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into four groups of particulates and each of 12 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the twelve flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 12 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, Activated Natural Killer (ANK) cells were delivered into a row of six wells by means of a micropipette. In each microtiter plate three rows of six wells each served as controls. The effector (ANK cells):target cell (tumor cells) ratio varied from 2.5:1 to 20:1. The ANK cells were exposed to the target cells for four hours. Subsequently, the wells were washed with Hanks Balanced Salt Solution and the number of ANK cells remaining in the wells was observed with a phase contrast microscope. This process was repeated until no ANK cells remained in the wells (usually 3 washes). Following removal of the ANK cells, the tumor cells were incubated in the wells for another 24 hours.

Cell number relative to control was determined. For the three tumor types increasing the effector:target cell ratio from 2.5:1 to 20:1 resulted in an increase in the number of tumor cells killed by the ANK cells.

EXAMPLE 3

Gene Therapy/Antisense Oligonucleotides

A 50 mg sample from a residual human mesothelioma was minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. The 50 mg sample was minced and was divided into four groups of particulates and each of four groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the four flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 4 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, antisense oligonucleotide for the urokinase-type plasminogen activator receptor (uPAR) was delivered to wells in the microtiter plate. Proteolysis of plasminogen to plasmin by urokinase-type plasminogen activator has been implicated in the processes of tumor cell proliferation and invasion. The concentrations of the uPAR antisense oligonucleotide were 1, 10 and 100 micromolar. uPAR sense and missense oligonucleotides at the concentrations of 1, 10 and 100 micromolar served as controls. The tumor cells were exposed to the oligonucleotides for 24 hours and then the agents were removed. The cells were allowed to incubate for another 72 hours so that inhibition of cell proliferation could be observed.

Cell number relative to control was then determined. Antisense oligbnucleotides to uPAR suppressed the proliferative activity of the tumor cells in a concentration dependent manner.

EXAMPLE 4

Combination Chemotherapy

Separate 50 mg samples from residual tissue from specimens from four human ovarian tumors were minced in medium with sterile scissors to a particle size of roughly 1 $mm^3$ and with a particle size distribution between about 0.25 and about 1.5 $mm^3$. The medium was Standard F-10 medium containing 17% calf serum and a standard amount of Penicillin and Streptomycin. Each 50 mg sample was minced and was divided into 4 groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, the chemotherapeutic agent Taxol was applied to the wells in the microtiter plates. The first three treatment rows in the plates (Rows 2, 3, and 4) were designed to have escalating Taxol doses (1.0, 5.0, and 25 $\mu$M) with a fixed carboplatin dose (200 $\mu$M). The last three treatment rows in the plates (Rows 6, 7, and 9) were designed to have a fixed Taxol dose (5 $\mu$M) with an escalating carboplatin dose (50, 200, and 1000 $\mu$M). Rows 5 and 9 served as a control. The Taxol exposure time was two hours. Twenty-four hours later, the cells in the wells were exposed to carboplatin for two hours. The tumor cells in the wells were then incubated for another 48 hours.

Cell number relative to control was determined. For the cells from the four tumor specimens a dose response relationship was observed for both the escalating Taxol/fixed carboplatin and fixed Taxol/escalating carboplatin treatment schema.

EXAMPLE 5

Hormonal Therapy

Separate 50 mg samples from residual tissue from specimens from four human breast tumors were minced in medium with sterile scissors to a particle size of roughly 1 mm$^3$ and with a particle size distribution between about 0.25 and about 1.5 mm. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-CO$_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, the antiestrogenic compound Tamoxifen was delivered to wells in the microtiter plates. A stock solution of Tamoxifen was initially prepared by dissolving 1.5 mg of Tamoxifen powder in 1 ml of absolute ethanol and then adding 9 ml of growth medium. This stock solution was then used to make Tamoxifen solutions in the concentration range of 10 nM to 20 $\mu$M. Six doses of Tamoxifen were used for cells from each of the four breast tumor specimens. An ethanol solution at a concentration equivalent to that at the highest Tamoxifen concentration served as a control. The tumor cells were exposed to Tamoxifen for 24 hours and then the agent was removed. The cells were allowed to incubate for another 72 hours so that inhibition of cell proliferation could be observed.

Cell number relative to control was then determined. There was no effect observed when the ethanol-only control wells were compared to the growth medium-only control wells. The cells of two of the four breast specimens tested showed an inhibition of cell proliferation by Tamoxifen exposure. These responses occurred in the mid to high Tamoxifen concentration ranges.

EXAMPLE 6

Differentiating Agent Therapy ("Biological Response Modification")

Separate 50 mg samples from residual tissue from specimens from four human breast tumors were minced in medium with sterile scissors to a particle size of roughly 1 mm$^3$ and with a particle size distribution between about 0.25 and about 1.5 mm$^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-CO$_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating the differentiating agent retinoic acid was delivered to wells in the microtiter plates. A stock solution of retinoic acid was initially prepared by dissolving retinoic acid powder in 1 ml of dimethyl sulfoxide (DMSO) and then adding 9 ml of growth medium. This stock solution was then used to make retinoic acid solutions in the concentration range of 0.1 to 1.0 mM. Six doses of retinoic acid were used for cells from each of the four breast tumor specimens. A DMSO solution at a concentration equivalent to that at the highest retinoic acid concentration served as a control. The tumor cells were exposed to retinoic acid for 24 hours and then the agent was removed. The cells were allowed to incubate for another 72 hours so that inhibition of cell proliferation could be observed.

Cell number relative to control was then determined. There was no effect observed when the DMSO-only control wells were compared to the growth medium-only control wells. The cells of three of the four breast specimens tested showed an inhibition of cell proliferation by retinoic acid exposure. These responses occurred in the mid to high retinoic acid concentration ranges.

EXAMPLE 7

Combined Modality Therapy Drug/Radiation

Separate 50 mg samples from residual tissue from specimens from two human brain tumors and two human ovarian tumors were minced in medium with sterile scissors to a particle size of roughly 1 mm$^3$ and with a particle size distribution between about 0.25 and about 1.5 mm$^3$. The medium was Standard F-10 medium containing 17% calf serum and a standard amount of Penicillin and Streptomycin. Each 50 mg sample was minced and was divided into four groups of particulates and each of 16 groups was charged to a separate labeled culture flask containing the above-described medium. Visual confirmation was made that the particulates were evenly distributed along the bottom of each flask and the flasks were placed in a 35° C., non-$CO_2$ incubator. Flasks were checked daily for growth and contamination. Over a period of a few weeks, with weekly removal and replacement of 5 ml of growth medium, the particulates grew into monolayers.

Enough cells were then removed from the monolayers grown in the flasks for centrifugation into standard size cell pellets for each of the 16 flasks. Each cell pellet was then suspended in 5 ml of the above-described medium and was mixed in a conical tube with a vortex for 6 to 10 seconds, followed by manual rocking back and forth 10 times. A 36 ml droplet from the center of each tube was then pipetted into one well of a 96-well microtiter plate together with an equal amount of trypan blue, plus stirring. The resulting admixture was then divided between two hemocytometer quadrants for examination using a standard light microscope. Cells were counted in two out of four hemocytometer quadrants, under 10× magnification—only those cells which had not taken up the trypan blue dye were counted. This process was repeated for the second counting chamber. An average cell count per chamber was calculated and by means known in the art the optimum concentration of cells in the medium was determined.

Accommodating the above calculations, additional cell aliquots from the 16 monolayers were separately suspended in growth medium via vortex and rocking and were loaded into a Terasaki dispenser adapted to a 60-well plate. Aliquots of the prepared cell suspension were delivered into the microtiter plates using Terasaki dispenser techniques known in the art. Cells were plated into 60-well microtiter plates at a concentration of 100 cells per well.

Twenty-four (24) hours post-plating, cells in the microtiter plate wells were exposed to the chemotherapeutic agent Taxol. One set of plates was designed to have escalating Taxol doses with (0.5–25.0 $\mu$M) with a fixed radiation dose (2 Gy). A second set of plates was designed to have a fixed Taxol dose (5 $\mu$M) with an escalating radiation dose (1 Gy–6 Gy). The cells in the plates were irradiated using a Siemans Stabilipan X-ray machine operating at 250 kVp, 15 mA with a dose rate of 75 rad/minute.

For each of the two treatment schema, cell number per well was monitored as a function of time through 5 days post-treatment. Cell number relative to controls was determined and survival curves were fit. A differential response among the cells from the four tumor specimens was observed. Both additive and synergistic cell killing was noted.

EXAMPLE 8

Initiation of a Prime Culture

A tumor biopsy of approximately 100 mg of non-necrotic, non-contaminated tissue was harvested from the patient by surgical biopsy and transferred to the laboratory in a standard shipping container. Biopsy sample preparation proceeded as follows. Reagent grade ethanol was used to wipe down the surface of a Laminar flow hood. The tumor was then removed, under sterile conditions, from its shipping container, and cut into quarters with a sterile scalpel. Using sterile forceps, each undivided tissue quarter was then placed in 3 ml sterile growth medium (Standard F-10 medium containing 17% calf serum and a standard amount of Penicillin and Streptomycin) and was systematically minced by using two sterile scalpels in a scissor-like motion. The tumor particulates each measured about 1 mm$^3$. After each tumor quarter was minced, the particles were plated in culture flasks using sterile pasteur pipettes (9 explants per T-25 or 20 particulates per T-75 flask). Each flask was then labeled with the patient's code, the date of explanation and any other distinguishing data. The explants were evenly distributed across the bottom surface of the flask, with initial inverted incubation in a 37° C. incubator for 5–10 minutes, followed by addition of about 5–10 ml sterile growth medium and further incubation in the - normal, non-inverted position. Flasks were placed in a 35° C., non-$CO_2$ incubator. Flasks were checked daily for growth and contamination. Over a period of a few weeks, with weekly removal and replacement of 5 ml of growth medium, the explants grew out into a monolayer.

EXAMPLE 9

Unified Tracking System a. Growth Rate

Following initiation of prime cell culture of a tumor specimen, the growth rate of the cells was determined until the chemosensitivity assay was performed. During this time period the growth was monitored by observing the percent of confluency of the cells in a flask. These data provide information valuable as a correlation to possible growth of the tumor in the patient as well as for the interpretation of the results of the chemosensitivity assay.

Figure 1B:
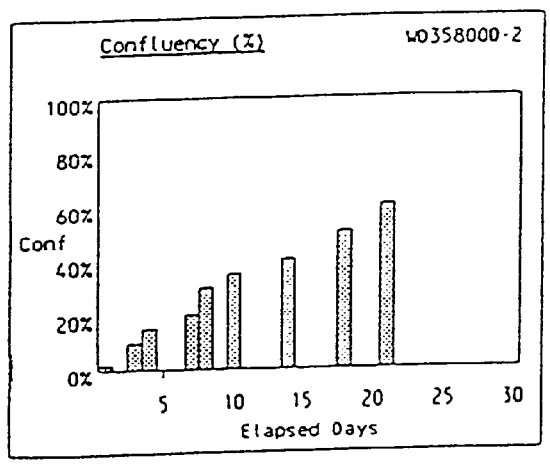
Figure 1C:
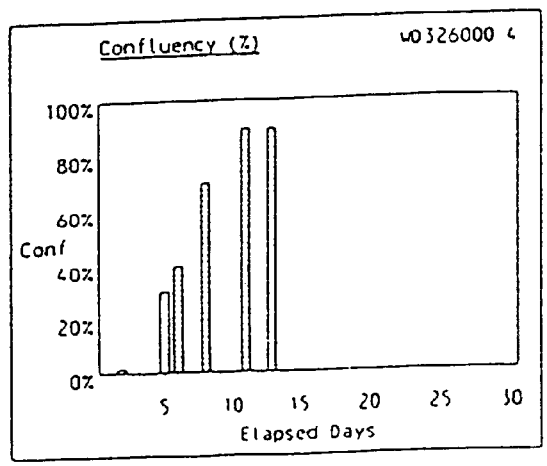
Figure 2A:
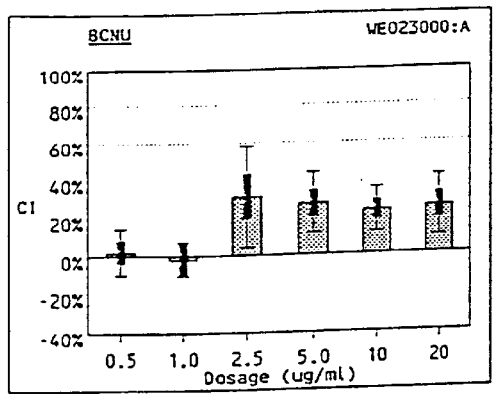
FIGS. 2A–2F through 5A–5F are graphs depicting the results of short-term and long-term chemotherapy assays.
Figure 2B:
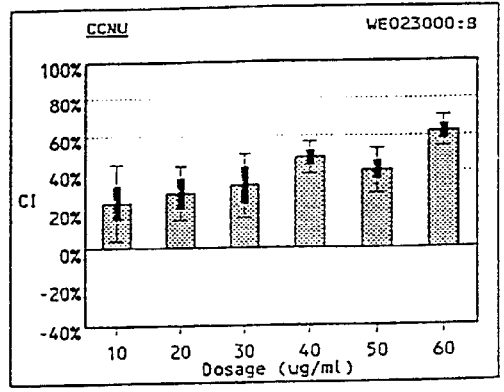
Figure 2C:
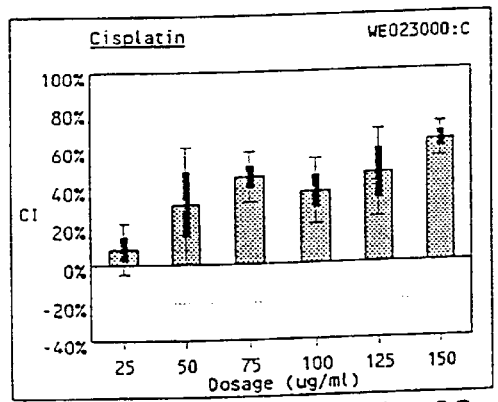
Figure 2D:
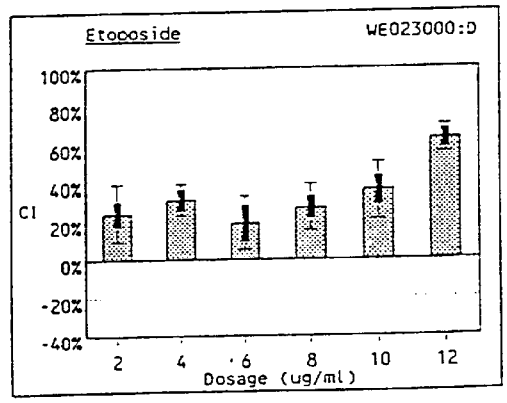
Figure 2E:
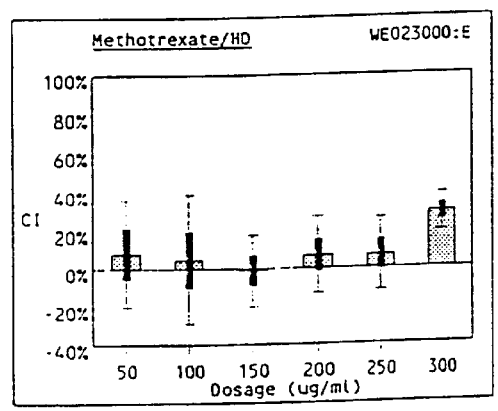
Figure 2F:
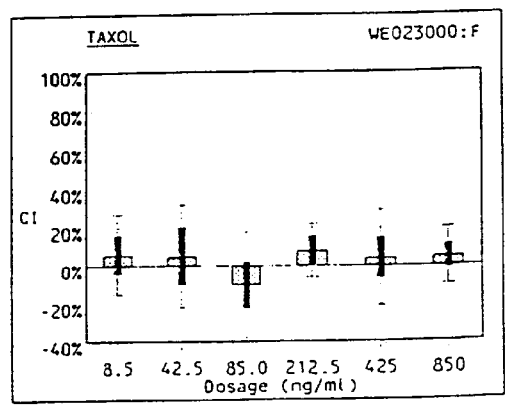
Figure 4A:
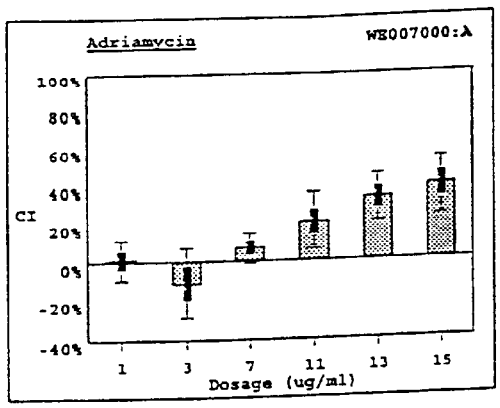
Figure 4B:
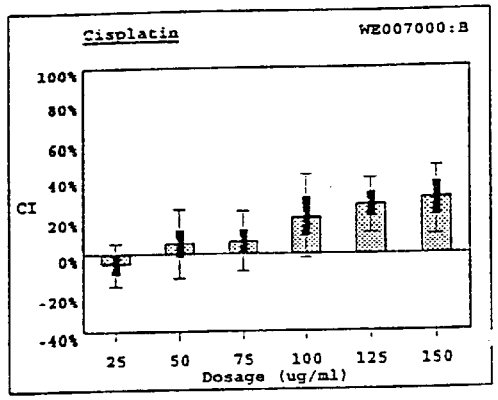
Figure 4C:
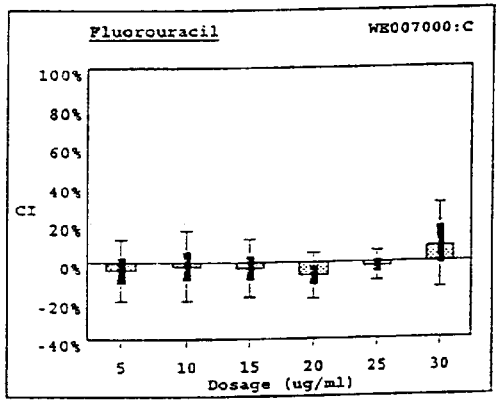
Figure 4D:
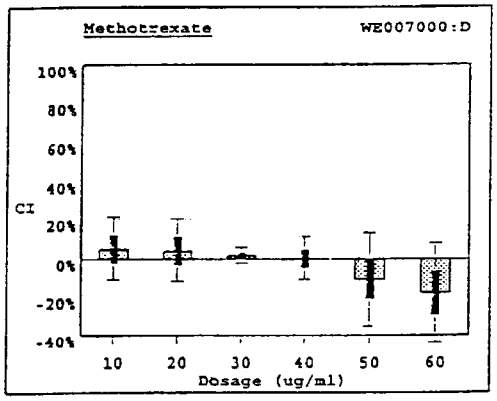
Figure 4E:
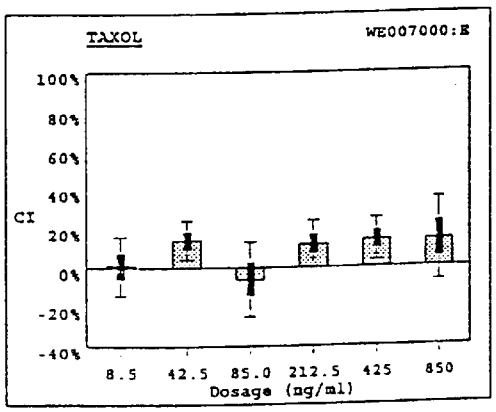
Figure 4F:
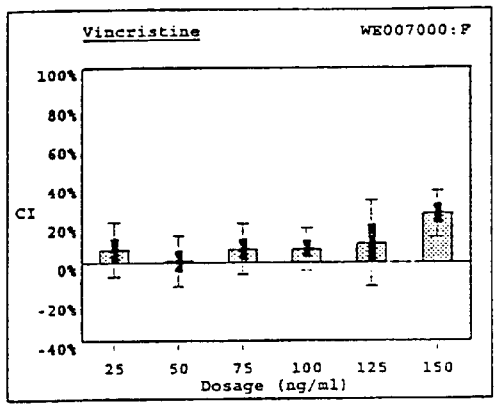
Figure 5A:
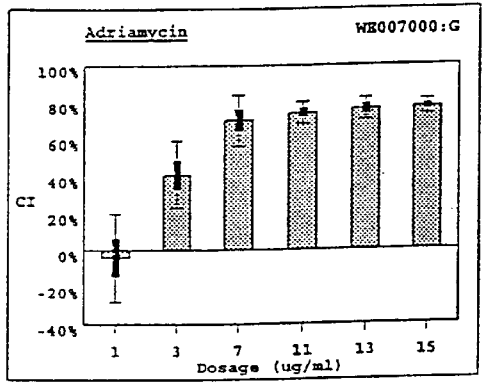
Figure 5B:
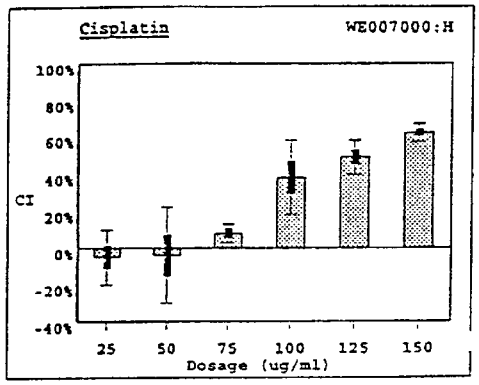
Figure 5C:
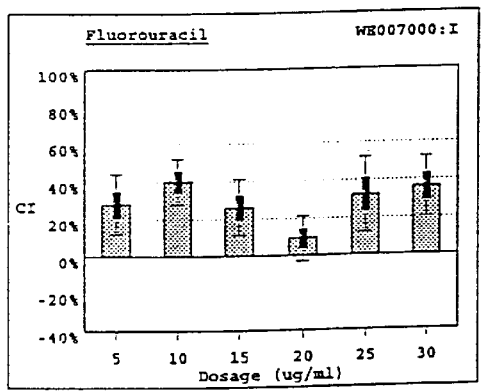
Figure 5D:
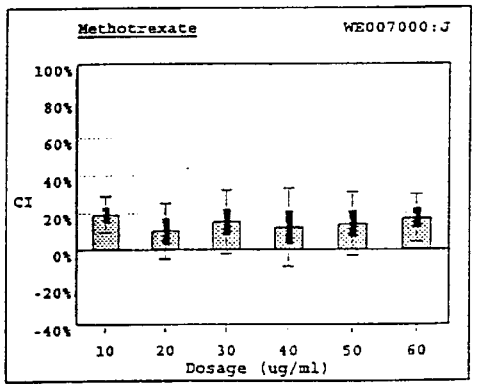
Figure 5E:
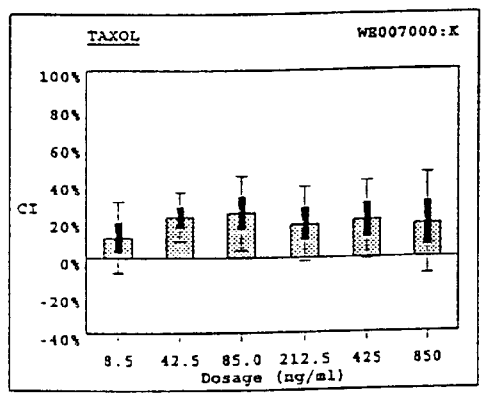
Figure 5F:
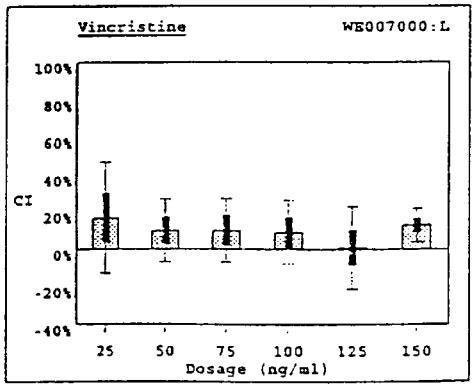

Three examples of growth rate data are shown in FIGS. 1A–1C. The percent of confluency of the cultured cells is plotted as a function of time after the initial seeding of the tissue specimen.

Slow Growth Rate (FIG. 1A): 25% confluent after 19 days
Moderate Growth Rate (FIG. 1B): 60% confluent after 21 days Fast Growth Rate (FIG. 1C): 90% confluent after 11 days b. Immunohistochemical Staining for Cell Characterization, etc.

Many tumor specimens will contain a mixture of cancer and normal cells. Although in many cases tumor cells will readily grow in tissue culture, while the normal cells will not, it is important to be able to distinguish the two cell types. Using immunoperoxidase techniques to stain cells for various intermediate filaments, the differences between normal (fibroblast-like) cells and cells from epithelial tumors were characterized. These techniques can also be used to identify other tumor cell characteristics which may have prognostic value.

An initial attempt at cultured cell characterization has been to use known epithelial tumor cell lines and a known fibroblast cell line. The epithelial tumor cell lines all have stained positively for a mixture ("cocktail") of epithelial intermediate filament antibodies, (not every line, however, has stained positively for the three antibodies within the mixture [AE1/AE3; Cam 5.2; EMA]). Some of the epithelial tumor cells in culture also stained mildly positive for an antibody against an intermediate filament characteristic of fibroblasts (vimentin). When staining for fibroblast intermediate filament (vimentin) in cell culture, all fibroblast cells were positive. Some focal staining by epithelial tumor cells for vimentin was also present.

|  | epithelial cocktail | vimentin |
| --- | --- | --- |
| epithelial tumor cells | ++ | + |
| fibroblasts | − | ++ |

Testing of intermediate filaments with antibodies for epithelial cells and vimentin appears to be a method of distinguishing certain characteristics of tumor and normal cells.

c. Response to Chemotherapy

The tissue culture chemosensitivity assay has been refined to make it more sensitive for the detection of damage produced by a variety of chemotherapeutic agents. The initial alteration was to allow a 24-hour time period between plating of cells in microtiter wells and the exposure to drugs. This time interval permits cells to be in an active state of proliferation, where they are more sensitive to cell cycle active agents. The second change was to initiate a long-term assay (growth inhibition assay) over a period of about 72 hours. The short-term assay is conducted 24–72 hours after the therapeutic agent is added. The longer time between drug exposure and assay allows for the detection of cell damage which occurs over a protracted period and requires several cell division cycles before it becomes apparent. "CI" is a measure of the relative survival rates of a given cell culture. It is calculated by according to the formula:

$$CI = \frac{(1 - \text{No. of cells in treated wells})}{\text{No. of cells in control wells}}$$

The data for a short-term assay and a long-term assay performed on two sets of patient cultured cells are presented in FIGS. 2A–2F through 5A–5F. The long-term assay (FIGS. 3A–3F and 5A–5F) may both accentuate a positive result obtained from the short-term assay (FIGS. 2A–2F and 4A–4F) and reveal an effect not observed during the short-term assay. The long-term assay is now incorporated into the tissue culture chemosensitivity on a routine basis.

d. Response to Radiation Therapy

The use of the microtiter well assay to analyze the direct effect of radiation therapy on tumor cells in culture has resulted in a rapid evaluation method for the determination of inherent cellular radiation response. As an example, two radiation dose-response curves generated from the microtiter well assay are presented in FIGS. 6 and 7. The cells from the tumor specimen in FIG. 6 are more resistant than those of the specimen in FIG. 7. The more resistant tumor has been previously irradiated.

The microtiter well assay is ideally suited for examination of the interaction of chemotherapeutic agents and radiation. Issues such as the differential sensitivity of drug/radiation combinations and the timing of drug/radiation combinations may be directly addressed with this system. An illustration of chemotherapeutic agent enhancement of radiation response is presented in FIGS. 8A–8C.

Figure 8A:
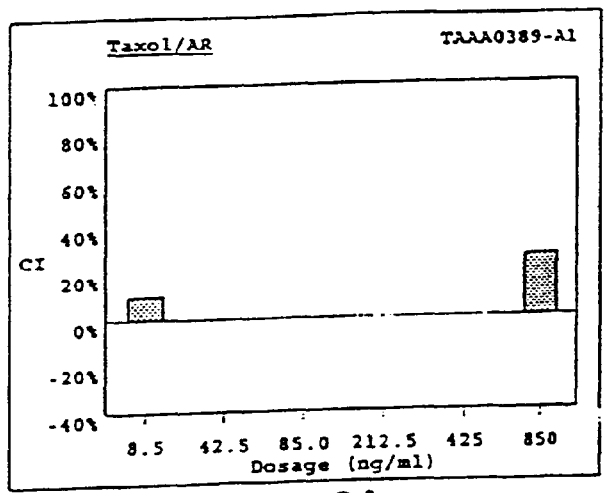
FIGS. 8A–8C are graphs of survival rates of cell cultures treated with radiation (FIG. 8A) or with radiation and Taxol (FIGS. 8B and 8C).
Figure 8B:
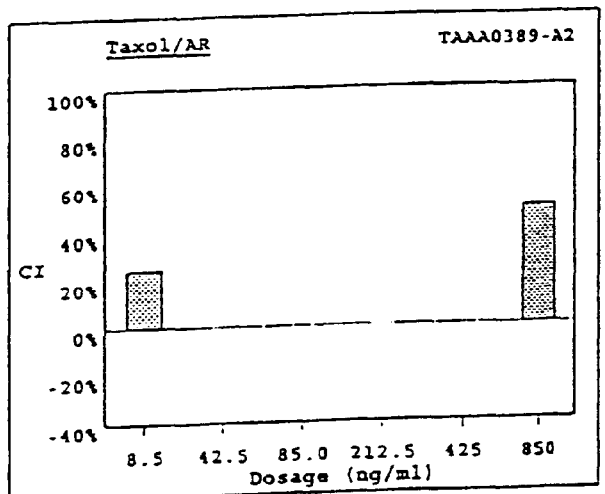
Figure 8C:
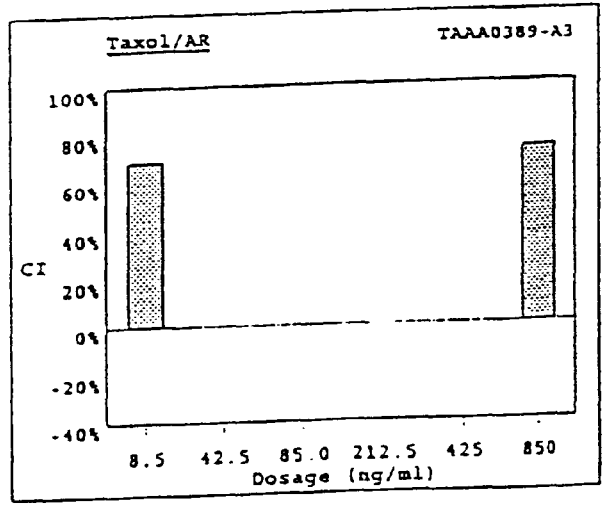

FIG. 8A: Radiation-only at 2 Gy and 4 Gy FIG. 8B: Taxol 8.5 ng/ml+2 Gy and 4 Gy FIG. 8C: Taxol 42.5 ng/ml+2 Gy and 4 Gy e. Response to Cellular Immunotherapy Activated lymphocytes are being used as a treatment for some types of cancer. These Activated Natural Killers (ANK) cells have been shown to mediate highly efficient cell killing for some tumor types. The microtiter well assay can be utilized to make a rapid assessment of ANK-induced tumor target cell killing. An illustration of two such interactions is presented in FIGS. 9A and 9B.

Figure 9A:
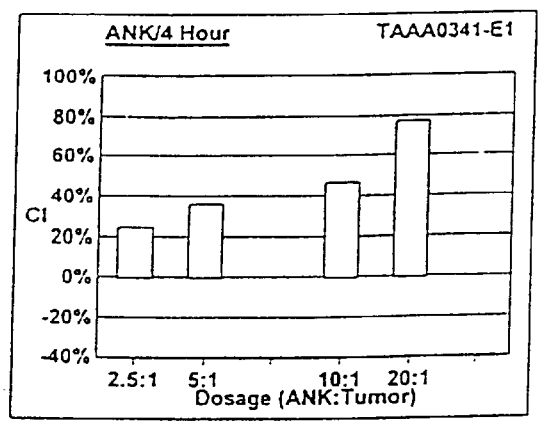
FIGS. 9A and 9B are graphs showing data from a series of experiments where target cells from two tumor types were exposed to Activated Natural Killer (ANK) cells.
Figure 9B:
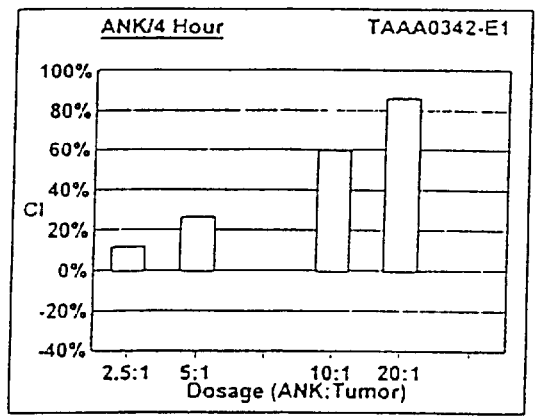

In FIGS. 9A and 9B, the target cells were from a melanoma and a renal carcinoma, respectively. The target cells were exposed to the ANK cells for 4 hours and then the assay was performed. The effector:target cell ratio varied from 1:20 to 1:2.5. The data show increasing cell killing as a function of increasing effector:target ratio.

f. Use of Tissue Culture Medium for Determination of Factors with Possible Prognostic/Biological Significance A number of substances secreted by tumor cells such as Tumor Associated Antigens and Plasminogen Activators and Inhibitors are believed to regulate a variety of processes involved in the progression of malignant disease. Many of these factors are produced by tumor cells growing in tissue culture and are secreted into the growth medium. The measurement of these factors in the medium from cell cultures of tumor specimens may prove to be of predictive value in the assessment of the biological behavior of individual cancers.

Preliminary work in this area has been on the detection of plasminogen activator inhibitor in the growth medium of glioblastoma cell lines. Plasminogen activator inhibitor expression has been shown to be increased in malignant brain tumors in patients. Medium from glioblastoma cell lines showed an increase in plasminogen activator inhibitor when compared to the medium alone.

Any or all of the steps of the unified assays and culturing techniques of the present invention may be automated. Indices can be automatically calculated by a computer which is programmed appropriately. Data can be input into the computer either manually or automatically, into a spreadsheet or database program, or the like. The spreadsheet or database program can be programed to reduce the data to the indices described above, or to any other relevant form, i.e., graphical or figurative representations of the data.

In one example, the cells to be assayed are grown on microtiter plates and assayed for their sensitivity to a chemotherapeutic agent according to the above-described protocols. The microtiter plates are read on an optical scanner and data from the scanner is automatically exported to a computer for calculation of a therapeutic index. Other types of scanners may be utilized depending upon the assay. For instance, a scanner for reading RIA data would be provided if the assay is an RIA assay.

Although the present invention has been described with respect to specific materials and methods above, the invention is only to be considered limited insofar as is set forth in the accompanying claims.

I claim:

1. A method of observing the behavior of cells derived from a sample of cancer cells, comprising:
   (a) collecting a specimen of a patient's malignant or hyperproliferative cells;
   (b) mechanically separating said specimen into cohesive multicellular particulates having a particle size between 0.25–1.5 mm$^3$;
   (c) growing a tissue culture monolayer from said multicellular particulates to form a prime culture which may be maintained;
   (d) forming at least one subculture of said prime culture for further analysis; and
   (e) monitoring said prime culture over a period of time for its characteristics to observe the behavior of the cells in said prime culture.

2. A method of observing the behavior of cells derived from a sample of cancer cells as claimed in claim 1, further comprising the step of maintaining the prime culture.

3. A method of observing the behavior of cells derived from a sample of cancer cells as claimed in claim 1, further comprising the steps of preparing a reference culture from the prime culture and treating the reference culture with one or more treatments as given to the patient.

4. A method of observing the behavior of cells derived from a sample of cancer cells as claimed in claim 3, further comprising the steps of preparing a subculture of one of the prime culture and the reference culture.

5. A method of observing the behavior of cells derived from a sample of cancer cells as claimed in claim 4, further comprising the step of assaying for a malignancy-specific marker in one of the prime culture, the reference culture, the subculture and tissue culture medium used to grow one of the prime culture, the reference culture or the subculture.

6. A method of observing the behavior of cells derived from a sample of cancer cells as claimed in claim 5, wherein the marker indicates one of aggressiveness and invasiveness of the cells in said prime culture.

7. A method of observing the behavior of cells derived from a sample of cancer cells as claimed in claim 6, wherein the marker is vascular endothelial growth factor.

8. A method of observing the behavior of cells derived from a sample of cancer cells as claimed in claim 5, wherein the marker is indicative of complications associated with the cells in said prime culture.

9. A method of observing the behavior of cells derived from a sample of cancer cells as claimed in claim 8, wherein the marker is indicative of a thrombogenic potential.

10. A method of observing the behavior of cells derived from a sample of cancer cells as claimed in claim 5, wherein the marker is identified by one of cytochemistry or immunohistochemistry.

11. A method of observing the behavior of cells derived from a sample of cancer cells as claimed in claim 10, wherein the marker is selected from the group consisting of an estrogen receptor, a progesterone receptor, an oncogene, a product of an oncogene, a marker for multi-drug resistance and a marker for phenotypic characterization.

12. A method of observing the behavior of cells derived from a sample of cancer cells as claimed in claim 5, wherein one or more of the steps are at least partially automated.

13. A method of observing the behavior of cells derived from a sample of cancer cells as claimed in claim 5, wherein the marker is characterized by a molecular biological technique.

14. A method of observing the behavior of cells derived from a sample of cancer cells as claimed in claim 13, wherein the molecular biological technique characterizes one of tumor cell heterogeneity or specific mutations of cancer-related genes.

15. A method of observing the behavior of cells derived from a sample of cancer cells as claimed in claim 2, further comprising the steps of:
   f. inoculating cells from one of the prime culture, the reference culture or a subculture of the prime culture or of the reference culture into a plurality of segregated sites; and
   g. treating the plurality of sites with at least one treating means, followed by assessment of sensitivity of cells in the site to the treating means.

16. A method of observing the behavior of cells derived from a sample of cancer cells as claimed in claim 15, wherein one or more of the steps are at least partially automated.

17. A method of observing the behavior of cells derived from a sample of cancer cells as claimed in claim 15, further comprising the step of phenotypically or genotypically analyzing the cells in one or more sites for drug resistance.

18. A method of observing the behavior of cells derived from a sample of cancer cells as claimed in claim 15, further comprising the steps of:
   h. collecting a specimen of a patient's non-malignant cells;
   i. separating the non-malignant cells into cohesive multicellular particulates;
   j. growing a tissue culture monolayer from the multicellular particulates of non-malignant cells to form a control culture;

k. inoculating the control culture in a plurality of non-segregated sites;

l. treating the plurality of segregated sites of the control culture with the same treating means as the segregated sites of the prime culture or a subculture thereof, followed by assessment of the sensitivity of the segregated cells of the control culture in the treating means; and m. comparing the sensitivity of the segregated cells of the prime culture or a subculture thereof with the sensitivity of the segregated cells of the control culture to the treating means.

19. A method of observing the behavior of cells derived from a sample of cancer cells as claimed in claim 18, wherein the assessment of steps g and l are calculations of the percentage or fraction of cells sensitive to the treatment and further comprising the step of:

n. creating a therapeutic index of a ratio of one of the percentage of or the fraction of sensitive cells or insensitive cells in the segregated cells of the control culture to one of the percentage of or the fraction of sensitive cells or insensitive cells in the segregated cells of the prime culture or subculture thereof.

20. A method of observing the behavior of cells derived from a sample of cancer cells as claimed in claim 19, further comprising the step of programming a computer to automatically perform calculations to create said therapeutic index.

21. A method of observing the behavior of cells derived from a sample of cancer cells as claimed in claim 20, wherein the segregated sites are in a readable plate having a plurality of culture wells and a scanner is used to automatically scan the segregated sites to determine the percentage or fraction of cells sensitive to the treatment and an interface is provided between the scanner and the computer allowing automated input of scanner data into the computer for calculation of the therapeutic index.

22. A method of observing the behavior of cells derived from a sample of cancer cells as claimed in claim 19, wherein the non-malignant cells are epithelial cells.

* * * * *